US012600701B2

(12) United States Patent
Adrián Rey et al.

(10) Patent No.: US 12,600,701 B2
(45) Date of Patent: Apr. 14, 2026

(54) N-ACYLHYDRAZONIC COMPOUNDS, USE IN THE TREATMENT OF AMYLOID AND NON-AMYLOID DEGENERATIVE AGGREGOPATHIES, AND PHARMACEUTICAL COMPOSITION

(71) Applicant: FACULDADES CATÓLICAS, Rio De Janeiro (BR)

(72) Inventors: Nicolás Adrián Rey, Rio de Janeiro (BR); Daphne Schneider Cukierman Rey, Rio de Janeiro (BR)

(73) Assignee: FACULDADES CATÓLICAS, Rio de Janeiro (BR)

( * ) Notice: Subject to any disclaimer, the term of this patent is extended or adjusted under 35 U.S.C. 154(b) by 718 days.

(21) Appl. No.: 17/912,427

(22) PCT Filed: Mar. 15, 2021

(86) PCT No.: PCT/BR2021/050107

§ 371 (c)(1),
(2) Date: Sep. 16, 2022

(87) PCT Pub. No.: WO2021/184097

PCT Pub. Date: Sep. 23, 2021

(65) Prior Publication Data

US 2023/0134773 A1 May 4, 2023

(30) Foreign Application Priority Data

Mar. 18, 2020 (BR) ...................... 10 2020 005423 6

(51) Int. Cl.
*C07D 233/64* (2006.01)
*C07D 401/12* (2006.01)
*C07D 405/12* (2006.01)
*C07D 409/12* (2006.01)

(52) U.S. Cl.
CPC ......... *C07D 233/64* (2013.01); *C07D 401/12* (2013.01); *C07D 405/12* (2013.01); *C07D 409/12* (2013.01)

(58) Field of Classification Search
CPC .. C07D 233/64; C07D 401/12; C07D 405/12; C07D 409/12
See application file for complete search history.

(56) References Cited

U.S. PATENT DOCUMENTS

2019/0106408 A1 4/2019 Rey et al.
2022/0064142 A1* 3/2022 Bond ................... C07D 333/22

FOREIGN PATENT DOCUMENTS

WO WO 2015/089599 A1 6/2015

OTHER PUBLICATIONS

STN Registry entry for CAS RAN 319462-68-5, Accessed from STNext, Entry date Feb. 2, 2001, Accessed May 4, 2025.*
Cukierman, Daphne S.; et al. \XI INH, an improved next-generation affinity-optimized hydrazonic ligand, attenuates abnormal copper(I)/copper(II)-a-Syn interactions and affects protein aggregation in a cellular model of synucleinopathy; Dalton Transactions (2020), 49(45), 16252-16267. May 11, 2020 (May 11, 2020).
E. Gaggelli, et al. Copper Homeostasis and Neurodegenerative Disorders (Alzheimer's, Prion, and Parkinson's Diseases and Amyotrophic Lateral Sclerosis); Chem. Rev. 2006, 106, 1995-2044. Jun. 1, 2006 (Jun. 1, 2006) item 4.6 from p. 2013, 3rd paragraph from the left column of the p. 2018, 1st paragraph from the right column from p. 2026 conclusion on the pp. 2038 and 2039.
International Search Report for PCT/BR2021/050107 mailed on Jun. 7, 2021.
Sathyadevi, P. et al.\ Novel ONN pincer type copper(II) hydrazide complexes: An investigation CmMar,(on the effect of electronegativity and ring size of heterocyclic hydrazides towards nucleic acid/protein binding, free radical scavenging and cytotoxicity; Inorgânica Chimica Acta 409 (2014) 185-194. Jan. 1, 2014 abstract compounds from scheme 1 on p. 186: synthesis 23.2 of the p. 186.
Srivastava, K. R; et al. Facile Eco-friendly Synthesis, Characterisation and Evaluation of Anti-microbial Activity of Cu(II) Complexes of Tridentate Ligands; Der Pharma Chemica, 2016, 8(3): 105-116. abstract, compound 1.2 and 1.4, pp. 105 and 106 copper complex synthesis on p. 107.
Written Opinion of the International Searching Authority for PCT/BR2021/050107 mailed on Jun. 7, 2021.

* cited by examiner

*Primary Examiner* — Alicia L Otton
(74) *Attorney, Agent, or Firm* — Birch, Stewart, Kolasch & Birch, LLP

(57) ABSTRACT

The present invention relates to a family of N-acylhydrazonic compounds structurally derived from 1-methyl-1H-imidazole-2-carboxaldehyde, or pharmaceutically acceptable salts thereof, and the use of said compounds to prevent and/or treat amyloid (such as Alzheimer's, Parkinson's and type 2 diabetes) and non-amyloid (such as cataracts) degenerative aggregopathies These compounds act as attenuators of the metal-protein interaction, preventing and/or decreasing protein oligomerization through competition with the target peptide or protein for the binding of physiological metal ions and, possibly, by modulating the protein-protein interaction itself. The invention also details four compounds specifically described as examples of N-acylhydrazones derived from 1-methyl-1H-imidazole-2-carboxaldehyde, namely: 1-methyl-1H-imidazole-2-carboxaldehyde isonicotinoyl hydrazone, 1-methyl-1H-imidazole-2-carboxaldehyde benzoyl hydrazone, 1-methyl-1H-imidazole-2-carboxaldehyde 2-furoyl hydrazone and 1-methyl-1H-imidazole-2-carboxaldehyde 2-thiophenyl hydrazone. The current application also comprises pharmaceutical compositions.

18 Claims, 8 Drawing Sheets

N-ACYLHYDRAZONIC COMPOUNDS, USE IN THE TREATMENT OF AMYLOID AND NON-AMYLOID DEGENERATIVE AGGREGOPATHIES, AND PHARMACEUTICAL COMPOSITION

FIELD OF INVENTION

The present invention refers to a series of new N-acylhydrazones structurally derived from 1-methyl-1H-imidazole-2-carboxaldehyde and their use. Particularly, the invention refers to the compounds themselves, as well as their uses and pharmaceutical compositions containing them, for the treatment of degenerative diseases.

In this sense, the object of the present invention is related to the treatment of amyloid degenerative aggregopathies, such as Alzheimer's and Parkinson's diseases, and type 2 diabetes, and non-amyloid aggregopathies, such as cataracts.

DESCRIPTION OF THE STATE OF THE ART

Currently, treatments available for Alzheimer's and Parkinson's diseases only slow down their progress, not being able to reverse the damage already suffered or to heal the patient. Type 2 diabetes mellitus is also a chronic and incurable disease, which mortality rate continues to increase in Brazil. Cataracts, in turn, is corrected by means of a surgical procedure. However, despite the great technological advances in the field of microsurgery, there are always great risks associated, in addition to the elevated costs of such a treatment.

In order to solve this issue, several proposals have been suggested and constitute the current state of the art, without them fitting into a treatment solution. In this sense, current research suggests that the partial or defective folding and aggregation of certain proteins are strongly associated with the development of degenerative aggregopathies, such as Alzheimer's and Parkinson's diseases, type 2 diabetes, and cataracts.

Based on non-native conformations, many copies of proteins aggregate to form, initially, soluble oligomers, and then insoluble fibers, or fibrils, causing these proteins to lose their physiological function and play pathological roles in the human body.

In this context, it is worth mentioning the amyloid fibers, which are protein deposits in antiparallel β-sheet conformation that, when together, can form mature, non-branched and rigid fibrils, which normally cannot be broken down through proteolysis, and present important synapto- and cytotoxicity.

Thus, the formation of amyloid fibers is associated with degenerative diseases, and the state of the art describes at least 27 proteins or polypeptides that are amyloid precursors, associated with diseases known as amyloidoses, the vast majority of which are neurodegenerative diseases. In various systemic amyloidoses, the final products of aggregation are insoluble amyloid deposits that affect the functioning of several organs.

Although these proteins and polypeptides differ in sequence, size and native conformations, certain characteristics of the aggregation process are quite similar. This fact makes it possible to propose a unique approach to prevent the aggregation and misfolding of the aforementioned proteins.

Most proteins initiate disturbances in their native conformation through the production of intermediates that are partially or defectively folded, which are highly prone to aggregate. Such intermediaries promote the association of monomers into soluble oligomers in the so-called nucleation phase, through intermolecular interactions.

Soluble oligomers, in turn, are generally rich in β-sheet and quickly convert into high molecular weight structures, known as protofibrils, during the exponential growth stage. Then, the protofibrils become elongated structures (fibrils) in the stationary phase.

Therefore, the stage of formation of early soluble oligomeric species is the determining step in the process of protofibrils formation, since such species are considered to be of greater toxicity and act as promoters of aggregation, from which fibrils and protofibrils grow on a nucleation-dependent manner.

In this context, the state of the art seeks solutions to prevent the formation of oligomers, treating and preventing degenerative diseases, as those mentioned above.

The brain is an organ that concentrates metal ions, whose levels increase as a result of physiological aging. Several studies indicate that metal dyshomeostasis can play a crucial role in a variety of age-related degenerative diseases. This led to the proposition that abnormal interactions between metals and different proteins may be one of the contributing elements to the etiologies of these disorders.

In more detail, the state of the art demonstrates that the main metal ions that act in the amyloid-β (Aβ) peptide aggregation process, associated to Alzheimer's disease, are copper(II) and zinc(II), which increase the aggregates' toxicity as well as the rate of aggregation of the peptide, acting primarily, though not exclusively, through the bonding to imidazole rings of histidine residues.

Still related to the mechanism of action of copper and zinc, it should be noted that both compete for the same amino acid residues of A. However, the role of copper is more relevant in terms of increasing the speed of aggregation, while zinc mainly induces conformational changes in the peptide.

Another relevant point is the fact that copper presents redox activity and, together with iron, increases oxidative stress in the brain through the production of reactive oxygen species (ROS), such as the hydroxyl radical and hydrogen peroxide, and reactive nitrogen species (RNS), like nitric oxide, through Fenton, Fenton-like and Haber-Weiss reactions. These unstable, short lived species attack biomolecules, causing damage to nucleic acids, membranes, proteins and lipids.

Regarding Parkinson's disease, the protein aggregation mechanism is related to the α-synuclein protein (α-Syn), pointed out as the main component of the inclusions known as Lewy bodies. Iron deposits were found in these inclusions, as well as an increase in copper concentration in the cerebrospinal fluid of patients with this disease. In addition, an analysis of the parkinsonian substantia nigra also revealed high amounts of zinc, but recently it has been shown that the interaction of this metal with α-Syn is very weak. Copper in contrast leads to efficient α-Syn aggregation and its selective fibrillation.

In the context of protein aggregation associated with Parkinson's disease, it has been shown that the protein deposits are intracellular and, inside the cells, copper is predominantly present in its reduced form, copper(I), which binds to α-Syn through three independent sites: Met-1/Met-5, His-50 and Met116/Met-127.

On the other hand, type 2 diabetes, a metabolic disorder related to insulin resistance, is also characterized as an amyloid disease, since denaturation and aggregation of amylin, or Islet Amyloid Polypeptide (IAPP), is observed. The aggregation of this protein into amyloid fibers makes it toxic to pancreatic β-cells.

In this context, the role of physiological metals, such as iron, copper and zinc, in the aggregation of amylin has also been extensively studied. The equilibrium between this polypeptide and zinc(II) is important for glycemic regulation since this metal ion is stored together with amylin in the β-cell granules. Currently, it is known that amyloid aggregation and disease progression occur when there is an imbalance between these two species. In addition to zinc(II), the interaction of amylin with copper(II) is capable of inducing the formation of oligomers and protofibrils.

With respect to cataracts, the state of the art shows that the levels of copper and zinc are elevated in the affected region (eyes' crystallin lens). Both copper(II) and zinc(II) quickly induce the non-amyloid aggregation of the γD-crystallin protein, the most abundant in the lens, forming high molecular weight aggregates. This aggregation is responsible for the opacity of the crystallin lens, which is the main feature of cataracts.

Since all these diseases present similar mechanisms related to protein aggregation, in which metal ions are involved, the use of a single therapy has been proposed, based on the mechanism of action of specific and selective sequestration of metal ions bound to peptides and proteins of interest. Such a strategy should not exhibit the deleterious effects of an indiscriminate chelation therapy, since these metal ions are should not be excreted, but rather redistributed in the brain of the patients, restoring the body's metal homeostasis.

Currently, the treatment of Alzheimer's disease, from light to moderate stages, is mainly based on the attempt to reduce the damage in the cholinergic system through the use of drugs that inhibit acetylcholinesterase, the enzyme responsible for the degradation of acetylcholine, which is the neurotransmitter whose presence in low amounts in patients results in cognitive deficit. In this context, the main drugs used are donepezil, rivastigmine and galantamine. When in a moderate to severe stage, patients with Alzheimer's disease are treated with an antagonist of the receptors of N-methyl-D-aspartate (NMDA), memantine, which regulates the activity of the cellular degeneration of glutamate, released in large quantities in the disease condition. Moreover, a combined pharmacological approach can be used. Despite being the treatment of choice in the excellency medical centers, the aforementioned drugs only delay the progress of the disease, not being able to reverse the damage already present, comprising, thus, a palliative set of treatments.

Regarding Parkinson's disease, the main treatment employed is the restitution of dopamine, through the use of levodopa, that is present in low concentrations in the patients' central nervous system due to the death of dopaminergic neurons. This is a prodrug that undergoes decarboxylation to become dopamine once it enters the brain. Despite improving the quality of life of patients through the inhibition of motor symptoms, this method does not represent an effective treatment for Parkinson's disease, in addition to having its effect decreased over time.

Type 2 diabetes, on the other hand, is also a chronic and incurable disease, which treatments are aimed at decreasing the production of glucose in the liver, increasing the sensitivity of the cells for insulin, and reducing the absorption of glucose by the intestine. These are again treatments that are not aimed at healing, and the mortality rate from this disease is still increasing, for example, in Brazil.

As mentioned above, with respect to the main treatment for the cataracts, it is explained that it occurs through a surgical procedure for removing the crystallin, in substitution with a new lens. Despite the great technological advances in the field of microsurgery, there is always a great risk associated to any operation, in addition to being a relatively expensive procedure for the patient and/or the public health system.

In this sense, one seeks constantly to better understand such pathologies and to develop new drug candidates that may reinforce the chemical arsenal of treatment and/or prevention of all these diseases. A new class of therapeutic agents with the potential to delay, or even prevent, the progression of the aforementioned degenerative diseases is the so-called Metal-Protein Attenuating Compounds (MPACs), which are polydentate ligands with moderate affinity for certain physiological metal ions. MPACs act in the reduction of the pathological oligomerization of proteins and peptides, in addition to reducing the oxidative stress, through the inhibition of the production of reactive oxygen species mediated by metal ions bound to these proteins.

In the state of the art regarding MPACs undergoing clinical trials for neurodegenerative diseases, clioquinol and its 8-hydroxyquinoline derivatives were initially considered promising. This lipophilic chelator is able to reduce the formation of amyloid plaques through a mechanism involving the removal of biometals. Although effective, the aforementioned compound presented, in clinical trials, serious side effects, which ended up preventing the use of this chelating agent in the treatment of neurodegenerative diseases. Another 8-hydroxyquinoline-derived compound is the PBT2 ligand, which is capable of reducing the aggregation of the Aβ peptide, limiting the toxicity of the oligomers and redistributing physiological metals in the brain on an animal model of Alzheimer's disease. When compared to clioquinol, PBT2 presents better penetration of the blood-brain barrier and was well tolerated by humans at daily oral doses of 50 to 250 mg in a 12-week study. However, despite the initially encouraging results, clinical trials were recently discontinued after the compound did not present the expected efficacy in Alzheimer's patients.

Next, the state of the art still presents the PBT434 ligand, evaluated in the context of Parkinson's disease, which is part of a new generation of substances belonging to the chemical group of quinazolinones.

All of these compounds present as the pharmacophore 8-hydroxyquinoline-derived moieties, a characteristic that may be at the center of the lack of clinical efficacy observed for these potential drugs so far.

Within this scope, it is worth noting that our research group demonstrated, a few years ago, the ability of an N-acylhydrazone derived from the 8-hydroxyquinoline moiety, the 8-hydroxyquinoline-2-carboxaldehyde isonicotinoyl hydrazone (INHHQ), in competing, in vitro, for the interactions with copper(II) and zinc(II) with the Aβ peptide and for the interactions with copper(II) and copper(I) with α-Syn.

Furthermore, in silico pharmacological analyses have shown that the compound is neutral in physiological pH and capable of crossing the blood-brain barrier, which has been experimentally proven through HPLC detection of the compound in the brain of rats intraperitoneally injected with INHHQ.

Acute toxicity assays were performed on healthy rats, as well as the study of an oxidative stress biomarker (GSH) and of the concentration of biometals in the animals exposed to this hydrazone. Results showed that INHHQ is non-toxic and does not act as a nonspecific chelating agent in rats with basal levels of metals.

In the anxiety and memory assays in mice, performed through tests of Elevated Plus Maze, Open Field and Novel Object Recognition, it was determined that INHHQ does not alter defensive responses related to fear and anxiety in healthy animals. In the same assays, it was demonstrated that the compound is capable of preventing short- and long-term memory damage induced by the intracerebroventricular infusion of Aβ oligomers in this experimental mice model.

In this sense, INHHQ represents a promising MPAC, becoming a potential treatment option for Alzheimer's and Parkinson's diseases, which can also be extrapolated to other copper and zinc-mediated aggregopathies.

Still in the context of its mechanism of action, it is important to emphasize that, despite the presence of the 8-hydroxyquinoline group in the structure of INHHQ, evidences suggest that the coordination of copper and zinc occurs through the N-acylhydrazonic system, an innovation that opens new perspectives in the development of promising Metal-Protein Attenuating Compounds.

Thus, the present invention is related to new N-acylhydrazones, structurally derived from 1-methyl-1H-imidazole-2-carboxaldehyde, with the potential to act on anomalous metal-protein interactions (MPAC activity) and, possibly, even protein-protein interactions relevant to the pathogenesis of degenerative aggregopathies, both amyloid and non-amyloid.

In addition, these enhanced analogues based on the INHHQ prototype have been projected through rationally thought changes in its structure, carried out in order to improve its physico-chemical and pharmacological properties, thus resulting in greater hydrophilicity and resistance towards hydrolysis.

The fact that the proposed compounds have the 1-methylimidazole ring gives them certain advantages over other previously described hydrazones, such as: increased water solubility and hydrolysis resistance; absence of tautomerism, which can lead to an increase in the yield of their preparation, when compared to other non-methylated imidazole derivatives; greater biocompatibility compared to a set of different heteroaromatic rings, such as pyridine; due to the change in the bite angles involved in the formation of chelating rings, an even better modulation of the affinity for biometals involved in protein aggregation processes is achieved, which leads to more subtle effects on the body, which is highly desirable in the present context.

With respect to the proposed, aiming at demonstrating the technical advantages of this application, it is necessary to analyze some already existing patent documents, in order to establish the advantages associated with the present invention.

The document EP1791818 (WO2006029850) describes hydrazonic derivatives and their use as beta secretase inhibitors but does not include derivatives of 1-methyl-1H-imidazole-2-carboxaldehyde. In addition, this document proposes such compounds to act as inhibitors of β-secretase, a class of enzymes involved in the first stage of Aβ peptide production in the brain. Although they aim at the same long-term objective, that is, the reduction of the accumulation of this peptide which is central for Alzheimer's disease, the document proposes a different mechanism of action, involving other biological targets. Another point to be highlighted is that the new compounds proposed in the present invention will not be limited to a possible treatment of Alzheimer's disease and can be applied to a wider range of degenerative diseases related to protein aggregation, amyloid or not, mediated by metal ions.

The document entitled WO2015109935, which deals with the preparation and use of compounds with a neural protective effect, in turn, despite mentioning imidazolyl substituents, does not specifically comprise the class of N-acylhydrazones. The compounds described in the cited patent present several activities, such as inhibition of monoamine oxidase, inhibition of cholinesterase, sequestration of free radicals and nerve protection. However, there is no mention to the capacity of these substances to bind to physiological metal ions and compete for these bonds with the proteins involved in the aforementioned pathologies, such as Alzheimer's and Parkinson's diseases.

The document U.S. Pat. No. 6,610,693 deals with antagonists and inhibitors of fructosamine oxidase and refers to this enzyme as a biological target to be inhibited for the treatment of type 2 diabetes. As compounds with such activity, the patent presents copper chelating agents and hydrazides. The chemical class of hydrazides is different from that of hydrazones, being the former, generally, the precursor in the synthesis of the latter. Hydrazides are compounds that present the functional group —$NHNH_2$, while hydrazones are produced by the reaction between hydrazides and carbonyl compounds, originating a Schiff-base-like bond, being characterized by the presence of the chemical group —HC═N—NH—, and, in the specific case of N-acylhydrazones, of the chemical group —HC═N—NH—CO—.

An important document is the one named WO2004087641, which deals with hydrazonic derivatives, proposing their use for the treatment and/or prevention of amyloidoses such as Alzheimer's, Parkinson's and type 2 diabetes. However, despite the apparent similarity with the subject described in the present invention, this document explores a distinct mechanism of action, not mentioning whatsoever the great chelating potential of these compounds as a method to avoid protein aggregation.

From the exposed, it can be concluded that the present invention deals, in fact, with new technology in the field of medicinal bioinorganic chemistry, in the sense that:

- It involves structurally unknown compounds, which is related to the use of the 2-(1-methylimidazole)-group as an aromatic substituent in the azomethine moiety of the proposed N-acylhydrazones;
- It suggests the prevention or decrease of protein oligomerization, both amyloid and non-amyloid, through competition with the target peptide or protein by binding to physiological metal ions and possibly by modulating the protein-protein interaction itself, affecting its oligomerization;
- It covers a wider range of potential pharmaceutical applications by targeting diseases related to protein aggregation (aggregopathies), both amyloidogenic (Alzheimer's, Parkinson's, type 2 diabetes, etc.) and non-amyloidogenic (cataracts, for example), which are mediated by physiological metals.

BRIEF DESCRIPTION OF THE INVENTION

The present invention is related to new compounds, structurally derived from the 1-methyl-1H-imidazole-2-carboxaldehyde, produced in order to act as MPACs, preventing and/or decreasing protein oligomerization, both amyloid and non-amyloid, through the competition with the target peptide or protein by binding to physiological metal ions and possibly by modulation of the protein-protein interaction itself. Particularly, such compounds can be used, among others, in the treatment and prevention of Alzheimer's, Parkinson's, type 2 diabetes and cataracts. However, their use is not necessarily restricted to this area.

The carbonylhydrazonic moiety (i.e., —HC═N—NH—CO—) was the pharmacophore chosen due to its coordination potential towards copper and zinc, which has already been proved effective in the competition with the Aβ peptide and the α-Syn protein.

It should be noted that carbonylated hydrazones have been described as coordinating metals through their azomethine nitrogen and carbonyl oxygen. This class of compounds is more stable regarding hydrolysis when compared to imines, since the C═N double bond of the azomethine is conjugated to the pair of electrons of the neighboring nitrogen which, through resonance, increases the negative charge density on the carbon atom, considerably reducing its electrophilicity.

Another point to be highlighted is the fact that the hydrazonic moiety is fixed, and the compounds described in the present invention contain the 1-methylimidazole ring. Such chemical group substantially increases the solubility of the hydrazones, in addition to making them more biocompatible. Methylation in one of the imidazole nitrogen atoms has, as the main goal, the simplification of the synthetic procedures, since the tautomerism present in this ring can make it difficult to isolate products and compromise their purity. Another advantage of the presence of this ring is related to the preferential protonation of the 1-methylimidazole group over that of the azomethine nitrogen, which prevents the activation of the azomethine carbon and protects the structural integrity of this family of N-acylhydrazones towards hydrolysis.

BRIEF DESCRIPTION OF THE FIGURES

The present invention will be described in more detail below, with reference to the attached figures which, in a schematic way and not limiting the inventive scope, represent examples of embodiment thereof. The illustrations are as follows.

DETAILED DESCRIPTION OF THE INVENTION

Figure 1:
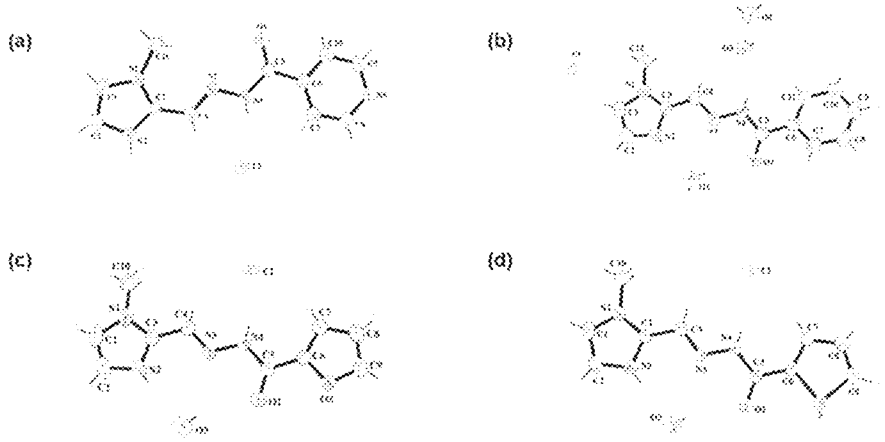
FIG. 1 displays the ORTEP (Oak Ridge Thermal Ellipsoid Plot) representation of compounds of formulae a) (IV), b) (V), c) (VI), and d) (VII). The ellipsoids were drawn at the 50% probability level.
Figure 2:
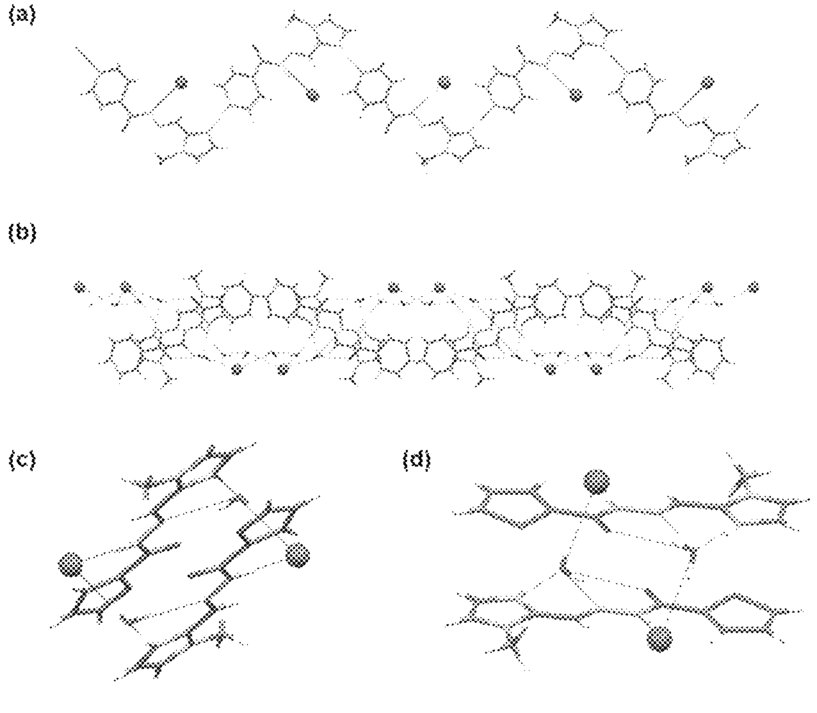
FIG. 2 shows the hydrogen bond interactions in compounds of formulae a) (IV), b) (V), c) (VI), and d) (VII).
Figure 3:
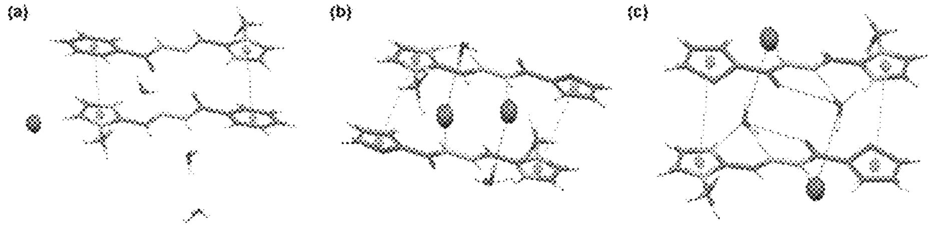
FIG. 3 presents the π-π stacking interactions in compounds of formulae a) (V), b) (VI), e c) (VII).
Figure 4:
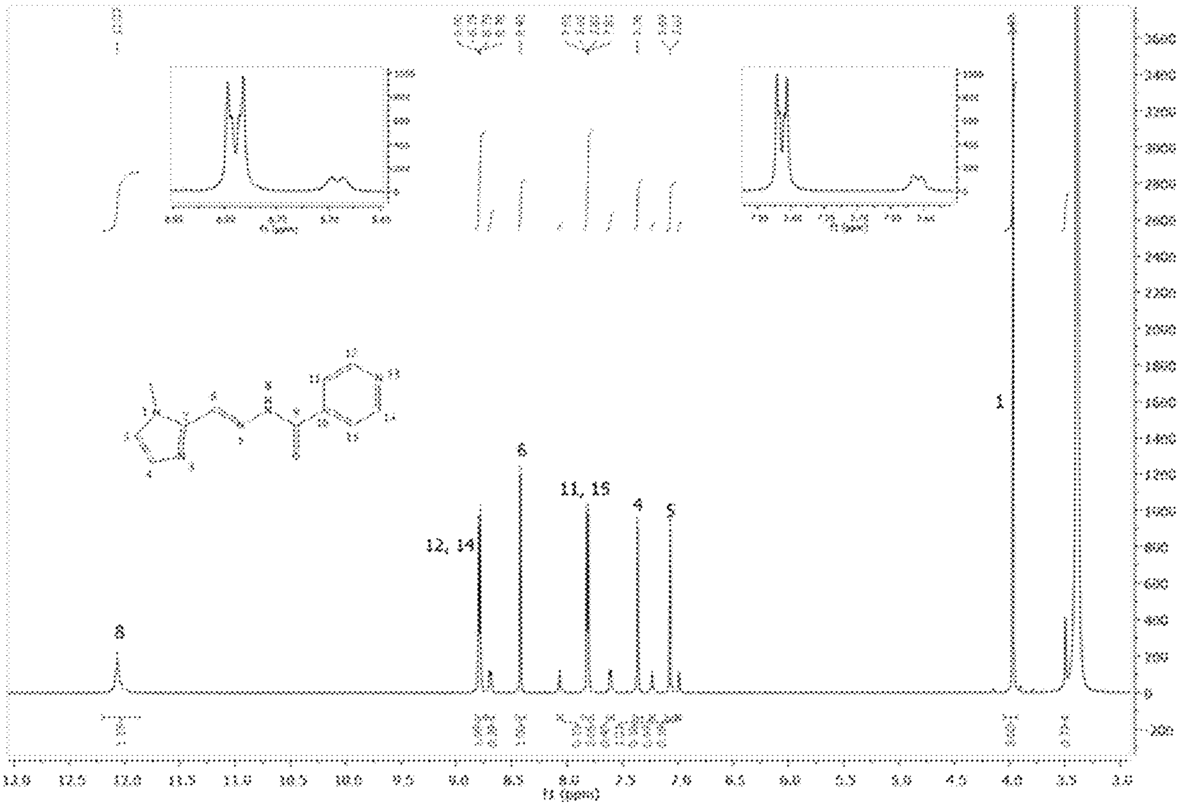
FIG. 4 shows the $^1H$ NMR spectrum (400 MHz) of the compound of formula (IV) in DMSO-$d_6$, at room temperature.
Figure 5:
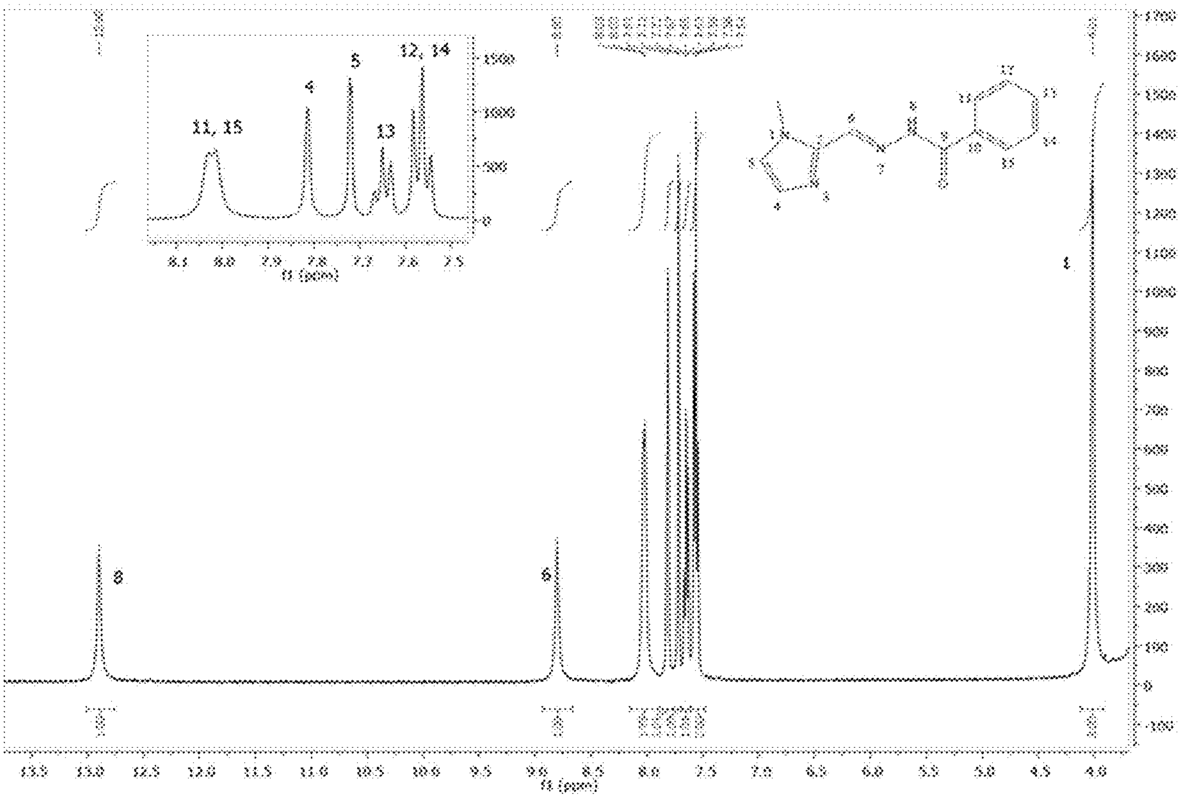
FIG. 5 shows the $^1H$ NMR spectrum (400 MHz) of the compound of formula (V) in DMSO-$d_6$, at room temperature.
Figure 6:
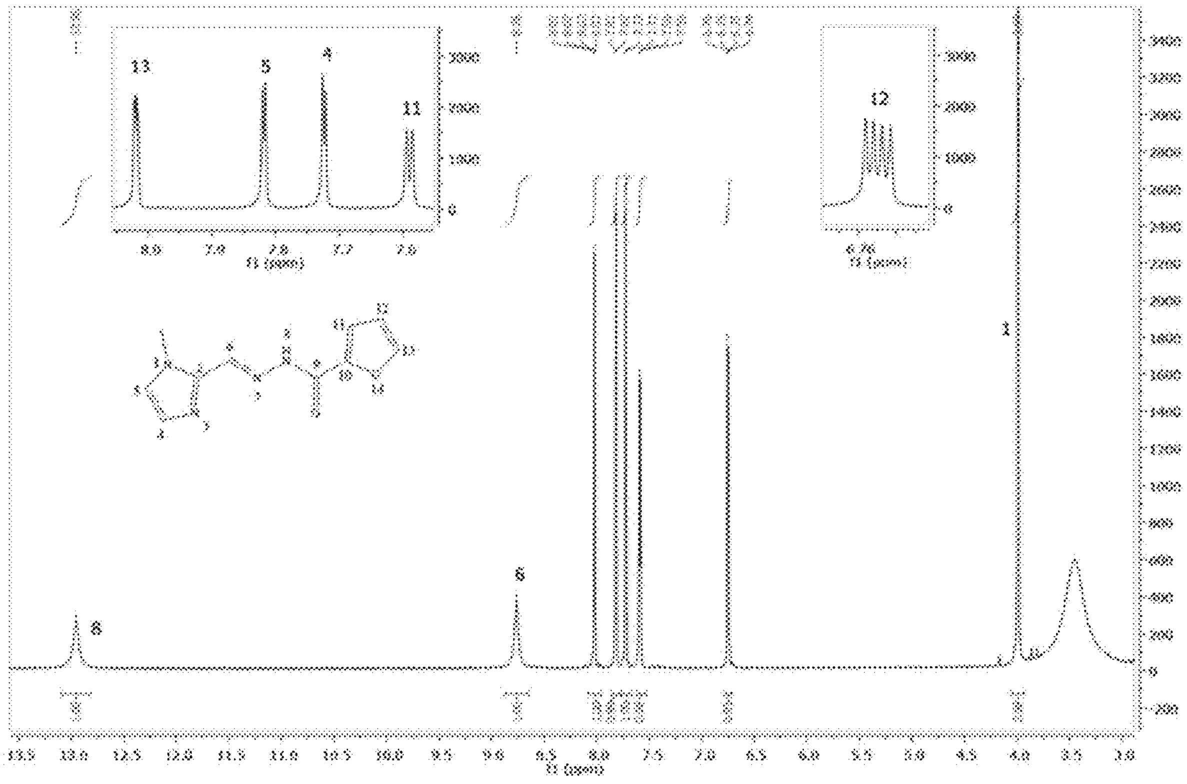
FIG. 6 shows the $^1H$ NMR spectrum (400 MHz) of the compound of formula (VI) in DMSO-$d_6$, at room temperature.
Figure 7:
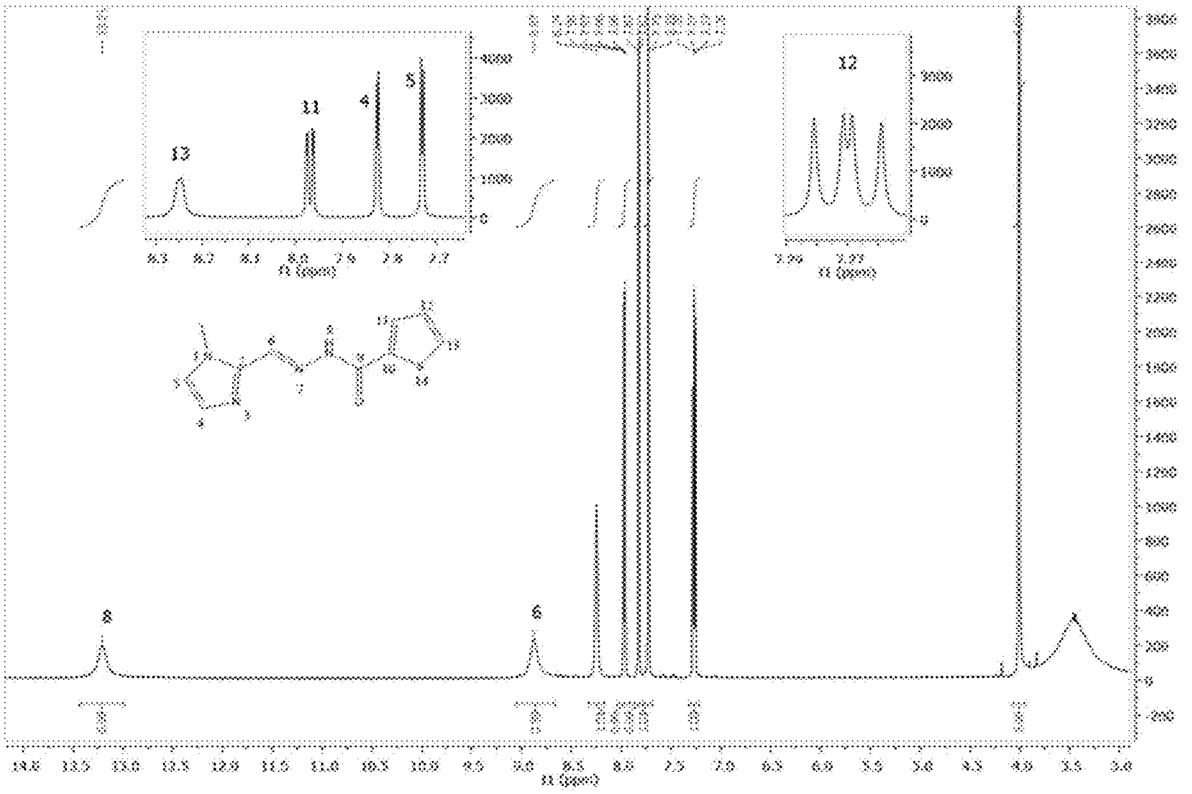
FIG. 7 shows the $^1H$ NMR spectrum (400 MHz) of the compound of formula (VII) in DMSO-$d_6$, at room temperature.

Unless defined otherwise, the technical and scientific terms used in connection with the present invention must have the meanings that are commonly understood by those skilled in the technique. The meaning and scope of the terms must certainly be intelligible; however, in the case of any latent ambiguity, the definitions provided herein take precedence over any extrinsic or dictionary definitions.

In this context, the present invention relates to a series of compounds belonging to the class of N-acylhydrazones and structurally derived from 1-methyl-1H-imidazole-2-carboxaldehyde, or even pharmaceutically acceptable salts thereof, with the general formula (I), as referenced below:

(I)

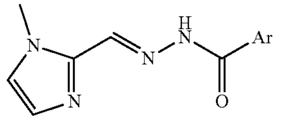

in which the Ar radical is a 5- or 6-membered heteroaromatic ring. The structure represented by formula (I) can be broken down into formulae (II) and (III):

(II)

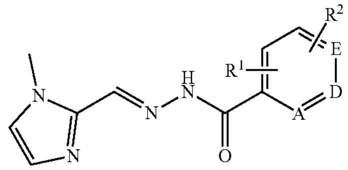

(III)

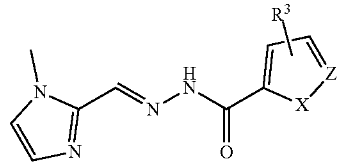

in which:

A represents the radicals $CR^4$ or N;
D represents the radicals $CR^4$ or N;
E represents the radicals $CR^4$ or N;
X represents the radicals O, S or NH;
Z represents the radicals $CR^4$ or N;

$R^1$ represents the radicals hydrogen (—H), halo (—F, —Cl, —Br, —I), alkyl (—$CH_3$, —$CH_2CH_3$, etc.), alkoxyl (—$OCH_3$, —$OCH_2CH_3$, etc.), ester [—C(═O)—$OCH_3$, etc.], acyl [—C(═O)—$CH_3$, etc.], phenoxyl (—OPh), cyano (—CN), nitro (—$NO_2$), hydroxyl (—OH) or thioalkoxyl (—$SCH_3$, —$SCH_2CH_3$, etc.);

$R^2$ represents the radicals hydrogen (—H), halo (—F, —Cl, —Br, —I), alkyl (—$CH_3$, —$CH_2CH_3$, etc.), alkoxyl (—$OCH_3$, —$OCH_2CH_3$, etc.), ester [—C(═O)—$OCH_3$, etc.], acyl [—C(═O)—$CH_3$, etc.], phenoxyl (—OPh), cyano (—CN), nitro (—$NO_2$), hydroxyl (—OH) or thioalkoxyl (—$SCH_3$, —$SCH_2CH_3$, etc.);

$R^3$ represents the radicals hydrogen (—H), halo (—F, —Cl, —Br, —I), alkyl (—$CH_3$, —$CH_2CH_3$, etc.), alkoxyl (—$OCH_3$, —$OCH_2CH_3$, etc.), ester [—C(═O)—$OCH_3$, etc.], acyl [—C(═O)—$CH_3$, etc.], phenoxyl (—OPh), cyano (—CN), nitro (—$NO_2$), hydroxyl (—OH) or thioalkoxyl (—$SCH_3$, —$SCH_2CH_3$, etc.);

e $R^4$ represents the radicals hydrogen (—H), halo (—F, —Cl, —Br, —I), alkyl (—$CH_3$, —$CH_2CH_3$, etc.), alkoxyl (—$OCH_3$, —$OCH_2CH_3$, etc.), ester [—C(═O)—$OCH_3$, etc.], acyl [—C(═O)—$CH_3$, etc.], phenoxyl (—OPh), cyano (—CN), nitro (—$NO_2$), hydroxyl (—OH) or thioalkoxyl (—$SCH_3$, —$SCH_2CH_3$, etc.).

It is important to note that the compounds described above through the formula (II) can present, in the positions represented by the letters A, D and E, a carbon atom bound to any of the groups defined by $R^4$ and/or the heteroatom nitrogen. Note that the maximum number of nitrogen atoms in the 6-membered ring is two.

It should also be noted that, for the compounds previously described by the formula (III), the position represented by the letter X can be occupied by an oxygen atom, a sulfur atom or by the NH group, and the position represented by the letter Z, by a carbon atom bound to any group defined by $R^4$ or the heteroatom nitrogen.

In a second modality, this invention specifically comprises the compounds of structural formulae (IV), (V), (VI) and (VII):

(IV)

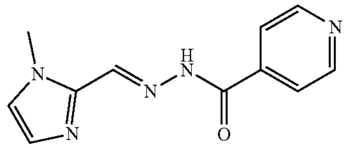

(V)

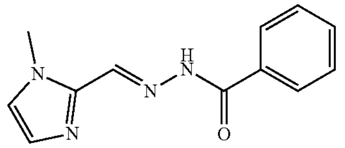

(VI)

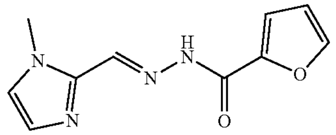

-continued (VII)

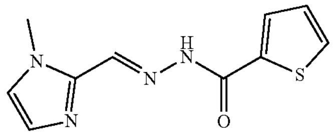

In this regard, it should be noted that compounds (IV) and (V) are derived from formula (II), by the substitutions A=D=$CR^4$, E=N e $R^1$=$R^2$=$R^4$=H (1-methyl-1H-imidazole-2-carboxaldehyde isonicotinoyl hydrazone) and A=D=E=$CR^4$ e $R^1$=$R^2$=$R^4$=H (1-methyl-1H-imidazole-2-carboxaldehyde benzoyl hydrazone), respectively.

It should also be noted that compounds (VI) and (VII) are derived from formula (III), through the substitutions X=O, Z=$CR^4$ e $R^3$=$R^4$=H (1-methyl-1H-imidazole carboxaldehyde 2-furoyl hydrazone) and X=S, Z=$CR^4$ e $R^3$=$R^4$=H (1-methyl-1H-imidazole-2-carboxaldehyde 2-thiophenyl hydrazone), respectively.

Still regarding the above examples, it should be noted that all the specific examples of formulae (II) and (III), namely compounds (IV), (V), (VI) and (VII) are N-acylhydrazones structurally derived from 1-methyl-1H-imidazole-2-carboxaldehyde.

For the purpose of detailing the aforementioned cases, some experimental data referring to N-acylhydrazones (IV), (V), (VI) and (VII) can be found below.

Synthesis: one universal way of synthesizing the N-acylhydrazones is through condensation reactions, which constitute a general class already well described in the literature, between 1-methyl-1H-imidazole-2-carboxaldehyde and different hydrazides. The aldehyde is weighed into a round bottom reaction flask and solubilized in ethanol. The hydrazide is weighed in order to attain a 1:1 molar ratio and solubilized in the same solvent, in a beaker. The hydrazide's solution is then dropwise added to the aldehyde, under constant stirring and mild heating. Drops of HCl are added to catalyze the reaction, and the mixture is kept under reflux for a few hours. The system is then cooled and warehoused at room temperature for slow evaporation of the solvent and precipitate formation. This, in turn, is filtered, washed with cold solvent and dried at room temperature. Single crystals can be isolated from the mother liquor, allowing for structural analysis through X-ray diffraction.

Melting points: The melting points of the compounds of formulae (IV), (V), (VI) and (VII) were determined in triplicate and used as a criterion of purity.

The determined values were:

(IV): 223±3° C.

(V): 128±1° C.

(VI): 153±2° C.

(VII): 215±2° C.

X-ray Crystallography: Table 1 presents some data on the crystals employed and others related to the collection and refinement of the structures. Selected bond distances and angles can be seen in Table 2. Table 3 summarizes geometric parameters of the H-bond interactions observed in crystal networks. On the other hand, the π-π stacking interactions are summarized in Table 4.

TABLE 1

Crystallographic data for compounds of formulae (IV), (V), (VI) and (VII).

| Compound | (IV) | (V) | (VI) | (VII) |
|---|---|---|---|---|
| Formula | $C_{11}H_{12}N_5OCl$ | $C_{12}H_{19}N_4O_4Cl$ | $C_{10}H_{13}N_4O_3Cl$ | $C_{10}H_{13}N_4O_2SCl$ |
| Formula weight (g $mol^{-1}$) | 265.71 | 318.76 | 272.69 | 288.75 |
| Crystal system | Monoclinic | Monoclinic | Monoclinic | Monoclinic |
| Space group | $P2_1$ | $P2_1/c$ | $P2_1/c$ | $P2_1/n$ |
| a (Å) | 4.3066 (4) | 9.4095 (6) | 8.4271 (2) | 7.0656 (4) |
| b (Å) | 17.7428 (11) | 23.9779 (10) | 18.8539 (5) | 18.0958 (6) |
| c (Å) | 8.1657 (5) | 7.4947 (5) | 8.2549 (2) | 10.6824 (4) |
| $\alpha = \gamma$ (°) | 90.00 | 90.00 | 90.00 | 90.00 |
| $\beta$ (°) | 102.475 (7) | 110.961 (8) | 102.381 (3) | 101.665 (4) |
| V ($Å^3$) | 609.22 (8) | 1579.05 (18) | 1281.07 (2) | 1337.67 (10) |
| Z | 2 | 4 | 4 | 4 |
| Temperature (K) | 293 (2) | 293 (2) | 293 (2) | 293 (2) |
| Crystal size (mm) | 0.12 × 0.26 × 0.54 | 0.42 × 0.52 × 1.00 | 0.34 × 0.60 × 1.08 | 0.26 × 0.52 × 1.01 |
| $\mu$(Mo K$\alpha$) ($mm^{-1}$) | 0.309 | 0.263 | 0.305 | 0.442 |
| Refl. measured/independent | 7384/3951 | 20662/4022 | 33691/3451 | 2331/3383 |
| $R_{int}$ | 0.0389 | 0.0322 | 0.0301 | 0.0363 |
| Parameters | 163 | 191 | 164 | 164 |
| $R_{obs}$ [$F_o > 2\sigma(F_o)$] | 0.0493 | 0.0436 | 0.0385 | 0.0344 |
| $R_{all}$ | 0.815 | 0.0668 | 0.0494 | 0.0480 |
| $wR_{obs}$ [$F_o^2 > 2\sigma(F_o)^2$] | 0.0919 | 0.1043 | 0.0985 | 0.0854 |
| $wR_{all}$ | 0.1077 | 0.1185 | 0.1036 | 0.0936 |
| S | 1.047 | 1.020 | 1.072 | 1.052 |
| $\Delta\rho_{max}$, $\Delta\rho_{min}$ (e $Å^{-3}$) | 0.262/−0.239 | 0.310/−0.226 | 0.263/−0.215 | 0.260/−0.215 |

TABLE 2

Selected geometric parameters for compounds (IV), (V), (VI) and (VII).

| | (IV) | (V) | (VI) | (VII) |
|---|---|---|---|---|
| Bond distance (Å) | | | | |
| C3—C4 | 1.449(4) | 1.447(2) | 1.445(2) | 1.442(2) |
| C4—N3 | 1.272(4) | 1.272(2) | 1.277(2) | 1.275(2) |
| N3—N4 | 1.272(4) | 1.356(2) | 1.277(2) | 1.356(2) |
| N4—C5 | 1.364(4) | 1.365(2) | 1.364(2) | 1.367(2) |
| C5—O1 | 1.217(4) | 1.223(2) | 1.220(2) | 1.221(2) |
| C5—C6 | 1.504(4) | 1.489(2) | 1.464(2) | 1.466(2) |
| Bond angle (°) | | | | |
| C3—C4—N3 | 120.0(3) | 115.6(1) | 116.6(1) | 116.3(1) |
| C4—N3—N4 | 115.3(2) | 118.2(1) | 117.1(1) | 117.3(1) |
| N3—N4—C5 | 117.5(2) | 117.6(1) | 117.1(1) | 117.0(1) |
| N4—C5—C6 | 115.3(2) | 116.4(1) | 113.8(1) | 115.4(1) |
| N4—C5—O1 | 123.1(3) | 121.5(1) | 123.0(2) | 122.5(1) |
| C6—C5—O1 | 121.6(3) | 122.5(1) | 123.2(1) | 122.2(1) |
| Torsion angle (°) | | | | |
| C3—C4—N3—N4 | 179.7(3) | −178.9(1) | 179.0(1) | 178.0(1) |
| C4—N3—N4—C5 | 177.1(3) | 176.7(1) | −179.1(1) | −178.5(1) |
| N3—N4—C5—C6 | 174.8(3) | −178.9(1) | −179.1(1) | 177.9(2) |
| N3—N4—C5—O1 | −4.7(5) | 1.2(2) | 2.9(2) | −2.6(2) |
| C7—C6—C5—O1 | 171.8(4) | −14.2(2) | 177.4(2) | 172.3(2) |

TABLE 3

Hydrogen bond geometric parameters for compounds (IV), (V), (VI) and (VII).

| D-H . . . A | D-H (Å) | H . . . A (Å) | D . . . A (Å) | D-H . . . A (°) |
|---|---|---|---|---|
| (IV) | | | | |
| N2—H2n . . . $N5^i$ | 1.02 | 1.74 | 2.754(4) | 171.0 |
| N4—H4n . . . Cl | 0.97 | 2.18 | 3.126(3) | 165.0 |

Symmetry code: $^i(1 - x, ½ + y, -z)$

TABLE 3-continued

Hydrogen bond geometric parameters for compounds (IV), (V), (VI) and (VII).

| D-H . . . A | D-H (Å) | H . . . A (Å) | D . . . A (Å) | D-H . . . A (°) |
|---|---|---|---|---|
| (V) | | | | |
| N2—H2n . . . O2 | 0.86 | 1.87 | 2.727(2) | 173.0 |
| N4—H4n . . . O3 | 0.80 | 2.05 | 2.818(2) | 159.0 |
| O2—H2a . . . $Cl^{i}$ | 0.91 | 2.22 | 3.130(2) | 174.0 |
| O2—H2b . . . O1 | 0.83 | 2.15 | 2.959(2) | 163.0 |
| O2—H2b . . . N3 | 0.83 | 2.47 | 2.975(2) | 120.0 |
| O3—H3a . . . O4 | 0.88 | 1.91 | 2.786(2) | 174.0 |
| O3—H3b . . . $Cl^{ii}$ | 0.85 | 2.30 | 3.141(2) | 170.0 |
| O4—H4a . . . $Cl^{iii}$ | 0.79 | 2.44 | 3.223(2) | 174.0 |
| O4—H4b . . . $Cl^{iv}$ | 0.84 | 2.34 | 3.178(2) | 174.0 |
| Symmetry code: $^{i}$(1 + x, y, z); $^{ii}$(−x, −y, −z); $^{iii}$(−x, ½ + y, ½ − z); $^{iv}$(−x, −y, 1 − z) | | | | |
| (VI) | | | | |
| N2—H2n . . . O3 | 0.86 | 1.93 | 2.775(2) | 169.0 |
| N4—H4n . . . Cl | 0.89 | 2.29 | 3.155(1) | 163.0 |
| O3—H3a . . . N3 | 0.82 | 2.43 | 3.025(2) | 130.0 |
| O3—H3a . . . O1 | 0.82 | 2.29 | 3.074(2) | 161.0 |
| O3—H3b . . . $Cl^{i}$ | 0.87 | 2.23 | 3.097(1) | 177.0 |
| Symmetry code: $^{i}$(1 − x, 1 − y, 1 − z) | | | | |
| (VII) | | | | |
| N2—H2n . . . O2 | 0.86 | 1.91 | 2.759(2) | 172.0 |
| N4—H4n . . . Cl | 0.85 | 2.37 | 3.193(1) | 166.0 |
| O2—H2a . . . N3 | 0.76 | 2.44 | 2.985(2) | 130.0 |
| O2—H2a . . . O1 | 0.76 | 2.30 | 3.021(2) | 160.0 |
| O2—H2b . . . $Cl^{i}$ | 0.86 | 2.34 | 3.216(1) | 172.0 |
| Symmetry code: $^{i}$(1 − x, −y, 1 −z) | | | | |

TABLE 4

Geometric π-π stacking parameters in compounds (V), (VI) and (VII).

| Compound | Centroid-centroid distance (Å) | Centroid-plane distance (Å) | Horizontal displacement (Å) |
|---|---|---|---|
| (V) | 3.532 | 3.449 | 0.76 |
| (VI) | 3.635 | 3.304 | 1.52 |
| (VII) | 3.632 | 3.392 | 1.30 |

Elemental analysis: The elemental analysis of carbon, hydrogen and nitrogen for compounds (IV), (V), (VI) and (VII) is detailed in Table 5, in which the calculated values for each formula and the experimental values obtained are presented.

TABLE 5

Elemental analysis of the described N-acylhydrazones.

| | C Calc | C Exp | H Calc | H Exp | N Calc | N Exp |
|---|---|---|---|---|---|---|
| (IV) $C_{11}H_{12}N_5OCl$ | 49.72% | 50.8% | 4.55% | 4.8% | 26.37% | 27.4% |
| (V) $C_{12}H_{19}N_4O_4Cl$ | 45.22% | 45.4% | 6.00% | 6.0% | 17.58% | 18.1% |
| (VI) $C_{10}H_{13}N_4O_3Cl$ | 44.05% | 43.7% | 4.80% | 4.8% | 20.55% | 20.5% |
| (VII) $C_{10}H_{13}N_4O_2SCl$ | 41.60% | 41.4% | 4.53% | 4.5% | 19.41% | 19.3% |

* Theoretical values calculated using the state of protonation, counter-ions and crystallization solvents observed in the respective structures.

$^1$H Nuclear Magnetic Resonance: Most hydrazones present, in their NMR spectra, different species in DMSO-$d_6$ solution. In theory, there are four possible configurations: a combination of the iminol and amido tautomers, and the geometric (E) and (Z) isomers. In practice, (Z) isomers are usually absent or present in very small amounts, due to their lower conformational stability.

Table 6 summarizes the assignments for the major set of signals present in the spectra of the synthesized hydrazones, according to the numbering scheme presented in FIGS. 4 to 7, which also present the respective one-dimensional $^1$H spectra.

TABLE 6

Assignments for the major sets of $^1$H NMR signals of the N-acylhydrazones.

| H/δ (ppm) | (IV) | (V) | (VI) | (VII) |
|---|---|---|---|---|
| 1 | 3.97 (s, 3H) | 4.01 (s, 3H) | 3.99 (s, 3H) | 4.01 (s, 3H) |
| 2 | — | — | — | — |
| 3 | — | — | — | — |
| 4 | 7.36 (s, 1H) | 7.81 (s, 1H) | 7.82 (d, 1H) | 7.83 (d, 1H) |
| 5 | 7.07 (d, 1H) | 7.72 (d, 1H) | 7.73 (d, 1H) | 7.73 (d, 1H) |
| 6 | 8.42 (s, 1H) | 8.80 (s, 1H) | 8.76 (s, 1H) | 8.87 (s, 1H) |
| 7 | — | — | — | — |

TABLE 6-continued

Assignments for the major sets of $^1H$ NMR signals of the N-acylhydrazones.

| H/δ (ppm) | (IV) | (V) | (VI) | (VII) |
|---|---|---|---|---|
| 8 | 12.07 (s, 1H) | 12.90 (s, 1H) | 12.96 (s, 1H) | 13.21 (s, 1H) |
| 9 | — | — | — | — |
| 10 | — | — | — | — |
| 11 | 7.81 (dd, 2H)* | 8.02 (d, 2H)* | 7.59 (d, 1H) | 7.97 (dd, 1H) |
| 12 | 8.79 (dd, 2H)** | 7.56 (t, 2H)** | 6.75 (dd, 1H) | 7.27 (dd, 1H) |
| 13 | — | 7.65 (t, 1H) | 8.02 (dd, 1H) | 8.25 (d, 1H) |
| 14 | ** | ** | — | — |
| 15 | * | * | — | — |

Computational calculation of pharmacologic parameters: In silico (theoretic) pharmacological analyzes allow to determine some characteristics of the compounds that are relevant in the development of a new drug. Lipinski's Rule of Five is used as a reference. Lipinski states that a good candidate for drug development has a limit of multiples of 5 as values for some parameters: log P less than or equal to 5, molecular weight (MW) less than or equal to 500, hydrogen bond acceptors (HBA) less than or equal to 10 and hydrogen bond donors (HBD) less than or equal to 5. The compound in question may have only one violation of these parameters to be considered a promising drug candidate. The rules allow, therefore, for a good theoretical prediction of the oral bioavailability profile and permeability of new substances.

The first analyzed parameter is the molecular weight (MW), related to the ease with which a drug can permeate the cell membrane. The lower the molecular weight, the more easily the molecule crosses membranes and can even pass through cellular pores or intracellular space. The second and third analyzed parameters are log P and log S. Log P, the partition coefficient, represents the hydrophilic-lipophilic balance of the molecule, while log S refers to the solubility of the compound in aqueous solution.

Such parameters combined are extremely important in the context of cellular permeability, since it is necessary that the drug does not have a very high lipophilicity, which would cause its retention in the highly lipophilic cellular space, nor a very high hydrophilicity, which would result in great difficulty to cross the lipid membranes.

The HBA and HBD parameters (Hydrogen Bond Acceptors and Hydrogen Bond Donors, respectively) are important because they assess the amount of hydrogen acceptors or donors in the molecule, aiming at the interaction with biological targets such as, for example, amyloidogenic proteins. Since hydrogen interactions play a fundamental role in the binding between proteins and small molecules, it is crucial for a drug to present an ideal balance between donors and receptors of these interactions when considering affinity for the molecular target.

PSA, in turn, is the polar surface area, which evaluates the degree of polarity of the molecule, that is, the greater the concentration of partial charges in some region of the molecule, the greater its hydrophilic character, which, in principle, would increase the solubility. However, it would hinder the ability of lipid penetration.

Another parameter that can be taken into account when evaluating a potential drug is called Druglikeness. This is a value determined by comparing fragments of the compounds with a database of commercially available compounds and with a database of non-drug compounds. The molecule in question is compared with 3,300 commercial drugs and 15,000 chemical substances.

Calculations were performed using the Osiris Property Explorer: DataWarior™ software. The new hydrazones are considerably more soluble (at least ten times) than INHHQ. The values calculated for their solubilities are shown in Table 7, together with the pharmacological parameters described above. All the new hydrazones have a partition coefficient (log P) within the ideal range to cross biological barriers, such as the blood-brain barrier, a characteristic that is crucial for the development of drugs that act at the brain. The greater solubility of the new ligands was verified experimentally.

TABLE 7

In silico pharmacological descriptors of N-acylhydrazones (IV), (V), (VI) and VII), and comparison with those calculated for INHHQ.

| Hidrazone | INHHQ | (IV) | (V) | (VI) | (VII) |
|---|---|---|---|---|---|
| MW | 292.30 | 229.24 | 228.25 | 218.22 | 234.28 |
| c log P | 2.2250 | 0.3832 | 1.3841 | 0.5728 | 1.2507 |
| c log S | −3.360 | −0.688 | −1.483 | −1.165 | −1.493 |
| HBA | 6 | 6 | 5 | 6 | 5 |
| HBD | 2 | 1 | 1 | 1 | 1 |
| PSA | 87.47 | 72.17 | 59.28 | 72.42 | 87.52 |
| Druglikeness | 4.42 | 5.85 | 5.85 | 5.77 | 7.43 |

Experimental octanol-water partition coefficient (log P): The experimental values of log P were determined for only some of the hydrazones in order to prove the accuracy of the computational calculations. Tris buffer $10^{-2}$ mol $L^{-1}$ pH 7.4 was used as the aqueous phase. Both phases were prepared separately, and contained the hydrazone of interest at low concentrations ($5\times10^{-5}$ mol $L^{-1}$). An ultraviolet/visible molecular absorption spectrum was acquired for each of the phases before mixing. The mixture was stirred at 37° C., protected from light. At the end of the incubation, the mixture was centrifuged for 10 minutes at 3000 rpm, and the layers were separated using pipettes. The concentrations in each phase were measured at the wavelength of greatest absorption of each hydrazone in the respective solvent, through calibration curves. Each compound was analyzed in triplicate and P was calculated as the average concentration ratio $C_o/C_a$ where $C_o$ is the concentration in the organic phase and $C_a$ in the aqueous phase.

Table 8 shows the experimental log P values obtained for the N-acylhydrazones of formulas (IV) and (V), and the calculated values, taken from Table 7, for comparison purposes. Experimental results were obtained using buffer with physiological pH, and the mixing and separation steps were performed at average human body temperature. This gives the experiment greater biological relevance compared to computational calculations. Even so, the values determined are in agreement with those calculated.

TABLE 8

| Experimental and calculated log P values for compounds (IV) and (V). | | |
|---|---|---|
| Hidrazone | Experimental | Calculated |
| (IV) | 0.67 ± 0.03 | 0.38 |
| (V) | 1.49 ± 0.13 | 1.38 |

Stability in aqueous solution containing 1% DMSO: Compounds were prepared at low concentrations ($5\times10^{-5}$ mol $L^{-1}$) in a solution containing 1% DMSO in ultra-pure water. Absorption spectra were obtained between 200 and 800 nm in a molecular absorption spectrophotometer at regular intervals over 12 hours. A final measurement was performed after four days. The room temperature was maintained at 17° C. throughout the experiment.

Figure 8:
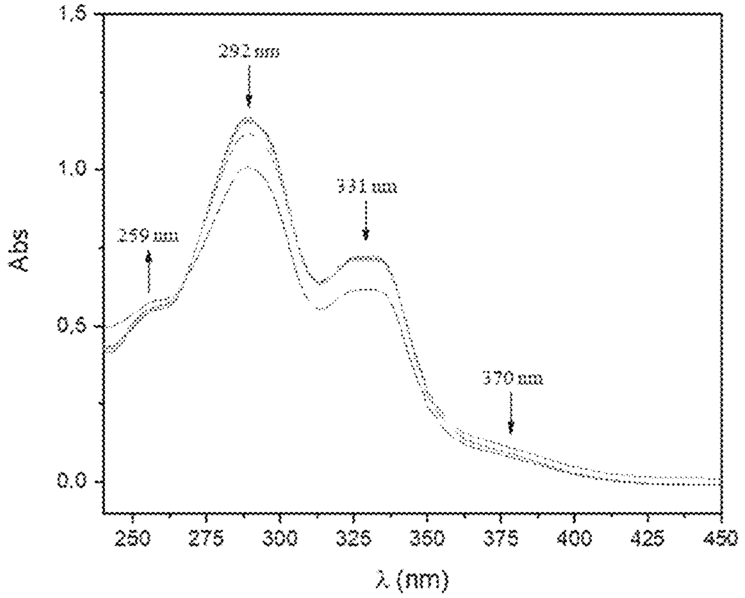
FIG. 8 displays the absorption spectra of INHHQ in a solution containing 1% DMSO/water ($5\times10^{-5}$ mol $L^{-1}$) at 17° C., over 4 days.

Under these conditions, and according to FIG. 8, INHHQ presents a decrease of approximately 12% in the intensity of its hydrazonic band at 292 nm over 4 days.

Figure 9:
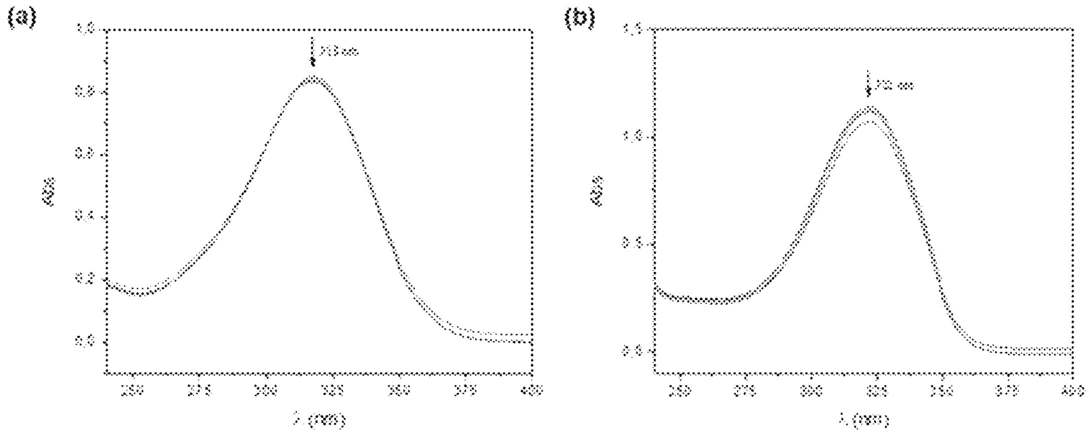
FIG. 9 shows the absorption spectra of the compounds of formulae a) (IV) and b) (VII) in a solution containing 1% DMSO/water ($5\times10^{-5}$ mol $L^{-1}$) at 17° C., over 4 days.

On the other hand, the new hydrazones derived from 1-methyl-1H-imidazole-2-carboxaldehyde are much more stable. The most stable compound, described by formula (IV), shows a decrease of less than 2% in the intensity of the absorption signal of the hydrazonic band, being extremely stable under these conditions. Representative hydrazone absorption spectra are shown in FIG. 9.

Figure 10:
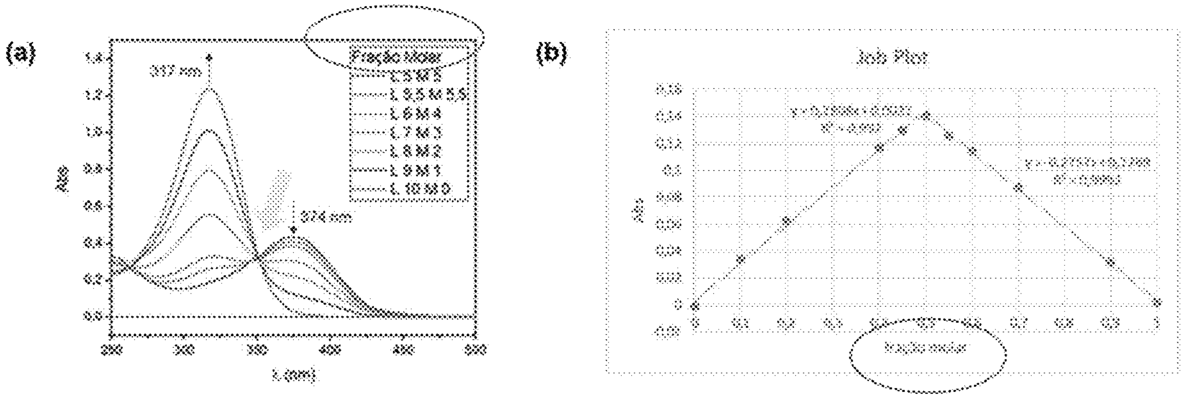
FIG. 10*a* presents ultraviolet/visible absorption spectra of mixtures of different molar fractions of the compound of formula (IV) and copper(II)
FIG. 10*b* displays a Job plot for this system at 374 nm.

Affinity constant for copper(II): The affinity constant of compound (IV) for copper(II) was determined using the Method of Continuous Variations, which consists of preparing mixtures of different molar fractions of ligand and metal, followed by measuring their UV-Vis absorbance. From these data, it is possible to calculate the stoichiometry of the complex generated, as well as its formation constant. FIG. 10*a* shows the spectra of the different metal-to-ligand ratios and the wavelengths of maximum absorption of the pure ligand (317 nm) and the complex (374 nm).

The presence of an isosbestic point indicates that there are only two absorbing species in equilibrium: the complex, formed in mixtures up to 0.5 molar fraction, and the excess of ligand that occurs in mixtures with higher molar fractions. This indicates that the ML-type complex (i.e., 1:1 stoichiometry) is formed preferentially under the conditions employed, which can be confirmed by the Job plot in FIG. 10*b*, which shows the maximum absorption at 374 nm occurring at the 0.5 molar fraction.

From this information it is possible to calculate the complex formation constant which, for the compound of formula (IV), has a value of 5.66±0.08 at 25° C. This value is approximately one thousand times lower than that presented by clioquinol under similar conditions, which indicates that the interaction with metal ions is more moderate for the N-acylhydrazone with formula (IV), as expected for an effective MPAC.

Figure 11:
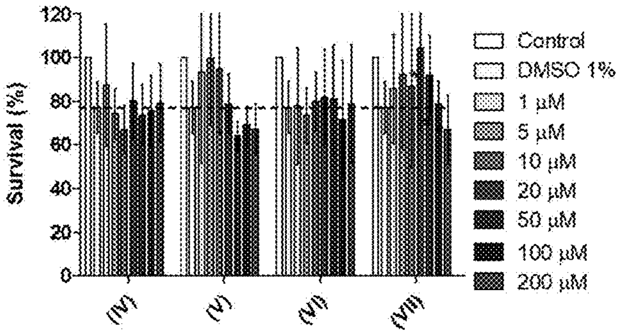
FIG. 11 presents the cytotoxicity of the N-acylhydrazones of formulae (IV), (V), (VI) and (VII) in H4 human neuroglioma cells.

Studies in H4 cells: The four exemplified compounds were tested in a human neuroglioma cell line (H4 cells) for their toxicity, through the MTT assay, which measures the metabolic activity of the cells by a reductive and colorimetric reaction of the reagent. FIG. 11 presents the results obtained in the form of percentage of cell survival. None of the 1-methyl-1H-imidazole-2-carboxaldehyde-derived hydrazones evaluated showed significant toxicity to these cells compared to the vehicle (culture medium containing 1% DMSO), all of which were less toxic than INHHQ.

Figure 12:
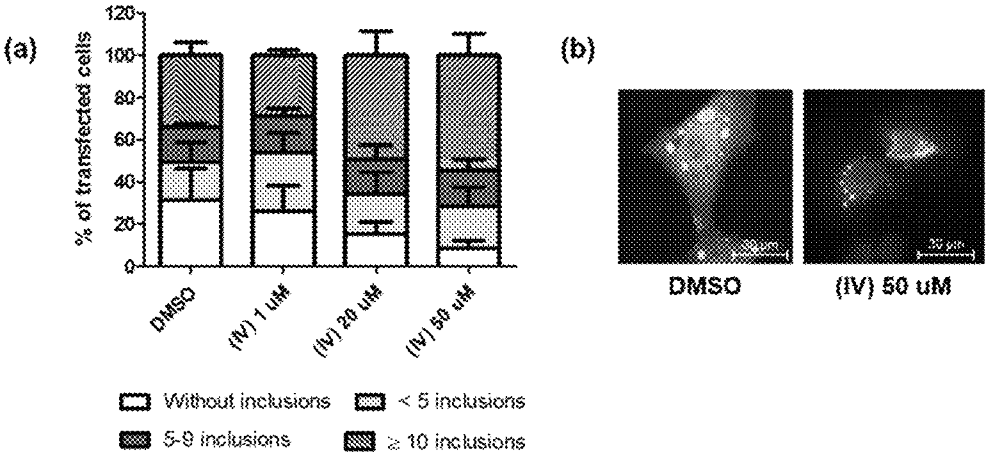
FIG. 12*a* shows the effect of the compound of formula (IV) on the cellular model of SynT-Sph1 aggregation in H4 cells by quantifying inclusions in transfected cells from images obtained by fluorescence microscopy.
FIG. 12*b* shows the effect of the compound of formula (IV) on the cellular model of SynT-Sph1 aggregation in H4 cells through representative images of the inclusions observed by fluorescence microscopy.

The isoniazid-derived hydrazone of formula (IV) was evaluated in greater detail in a cellular model of α-synuclein aggregation in H4 cells. This model consists of the co-transfection of an α-synuclein construct containing the first 83 amino acids of the EGFP protein linked to its C-terminal portion (SynT) with the synphilin-1 protein (Sph1), resulting in positive inclusions for α-Syn which can be observed by fluorescence microscopy after immunostaining. This compound showed a significant effect on the amount of cells without inclusions and with more than 10 inclusions (FIG. 12*a*) and also on the sizes of inclusions observed (FIG. 12*b*). It was also found that the compound does not change the levels of α-Syn expression, and that its effect is directly related to the quaternary structure of the aggregates, having a direct impact on their morphology, which are less compact after treatment.

With respect to its application, the present invention refers, at first, to the use of the family of compounds defined above by formulas (II) and (III) as attenuators of anomalous metal-protein interactions, since they are chelators with moderate affinity for certain physiological metal ions. Such compounds act in the inhibition of defective folding and protein aggregation, preventing and treating degenerative aggregopathies, such as Alzheimer's and Parkinson's diseases, type 2 diabetes and cataracts.

The term "treatment" as used herein, unless otherwise indicated, includes the treatment of Alzheimer's disease, Parkinson's disease, type 2 diabetes and cataracts, which comprises administering a therapeutically effective amount of the compounds defined by formulas (II) or (III).

In yet another aspect, the present invention also deals with any pharmaceutical compositions containing a therapeutically effective amount of any of the compounds defined by formulas (II) or (III), of which (IV), (V), (VI), (VII) are examples, and at least one pharmaceutically acceptable excipient, in which the N-acylhydrazone in question is the active component.

It is also noteworthy that, since the entire family of compounds described by formulas (II) and (III) is unprecedented, other potential uses, not detailed in the present patent application, are also part of the scope of the present invention. Those skilled in the art will appreciate that numerous variations regarding the scope of protection of the application are permitted and, thus, it reinforces the fact that the present invention is not limited to the particular configurations/embodiments described above.

The invention claimed is:

1. An N-acylhydrazonic compound, structurally derived from 1-methyl-1H-imidazole-2-carboxaldehyde, or a pharmaceutically acceptable salt thereof, having the following formula (I):

(I)

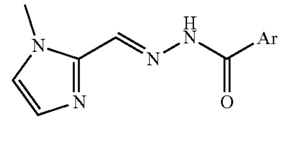

in which Ar is a 5- or 6-membered heteroaromatic ring.

2. The N-acylhydrazonic compound according to claim 1, having the following formulae (II) or (III):

(II)

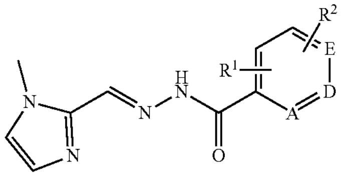

(III)

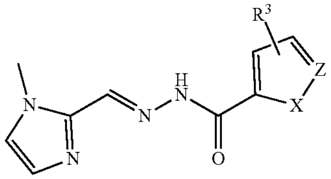

in which:

A represents $CR^4$ or N;

D represents $CR^4$ or N;

E represents $CR^4$ or N;

X represents O, S or NH;

Z represents $CR^4$ or N;

$R^1$ represents a hydrogen, a halogen, an alkyl group, an alkoxyl group, an ester group, an acyl group, a phenoxyl group, a cyano group, a nitro group, a hydroxyl group, or a thioalkoxyl group;

$R^2$ represents a hydrogen, a halogen, an alkyl group, an alkoxyl group, an ester group, an acyl group, a phenoxyl group, a cyano group, a nitro group, a hydroxyl group, or a thioalkoxyl group;

$R^3$ represents a hydrogen, a halogen, an alkyl group, an alkoxyl group, an ester group, an acyl group, a phenoxyl group, a cyano group, a nitro group, a hydroxyl group, or a thioalkoxyl group; and $R^4$ represents a hydrogen, a halogen, an alkyl group, an alkoxyl group, an ester group, an acyl group, a phenoxyl group, a cyano group, a nitro group, a hydroxyl group, or a thioalkoxyl group, or a pharmaceutically acceptable salt thereof, with the proviso that at least one of A, D or E represents N.

3. The N-acylhydrazonic compound according to claim 2, wherein A, D and E represent a number of nitrogen heteroatoms not more than two, or a pharmaceutically acceptable salt thereof.

4. The N-acylhydrazonic compound according to claim 2, wherein $A=D=CR^4$, E=N and $R^1=R^2=R^4=H$, which structure is represented by the formula (IV):

(IV)

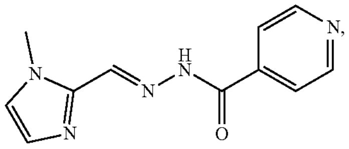

or a pharmaceutically acceptable salt thereof.

5. The N-acylhydrazonic compound according to claim 2, wherein X=O, $Z=CR^4$ and $R^3=R^4=H$, which structure is represented by the formula (VI):

(VI)

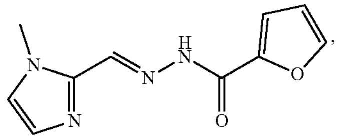

or a pharmaceutically acceptable salt thereof.

6. The N-acylhydrazonic compound according to claim 2, wherein X=S, $Z=CR^4$ and $R^3=R^4=H$, which structure is represented by the formula (VII):

(VII)

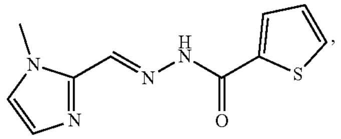

or a pharmaceutically acceptable salt thereof.

7. A method for treating amyloid or non-amyloid degenerative aggregopathy, comprising:

administering, to a subject in need thereof, the N-acylhydrazonic compound of formula (I) as defined in claim 1, or a pharmaceutically acceptable salt thereof, as an active component.

8. The method according to claim 7, wherein the amyloid or non-amyloid degenerative aggregopathy is Alzheimer's, Parkinson's, type 2 diabetes, or cataracts.

9. The method according to claim 7, wherein said N-acylhydrazonic compound is a compound represented by the following formulae (II) or (III):

(II)

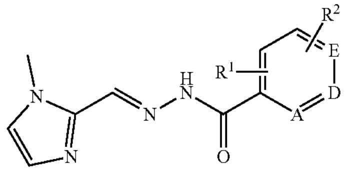

(III)

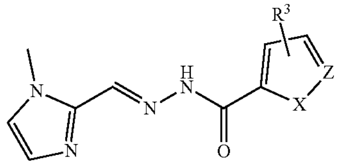

in which:

A represents $CR^4$ or N;

D represents $CR^4$ or N;

E represents $CR^4$ or N;

X represents O, S or NH;

Z represents $CR^4$ or N;

$R^1$ represents a hydrogen, a halogen, an alkyl group, an alkoxyl group, an ester group, an acyl group, a phenoxyl group, a cyano group, a nitro group, a hydroxyl group, or a thioalkoxyl group;

$R^2$ represents a hydrogen, a halogen, an alkyl group, an alkoxyl group, an ester group, an acyl group, a phenoxyl group, a cyano group, a nitro group, a hydroxyl group, or a thioalkoxyl group;

$R^3$ represents a hydrogen, a halogen, an alkyl group, an alkoxyl group, an ester group, an acyl group, a phenoxyl group, a cyano group, a nitro group, a hydroxyl group, or a thioalkoxyl group; and $R^4$ a hydrogen, a halogen, an alkyl group, an alkoxyl group, an ester group, an acyl group, a phenoxyl group, a cyano group, a nitro group, a hydroxyl group, or a thioalkoxyl group, or a pharmaceutically acceptable salt thereof, with the proviso that at least one of A, D or E represents N.

10. The method according to claim 9, wherein said compounds of formulas (II) or (III) are selected between those represented by the formulae (IV), (VI) or (VII):

(IV)

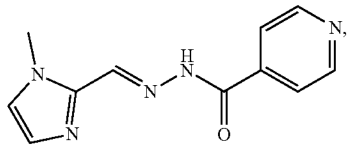

(VI)

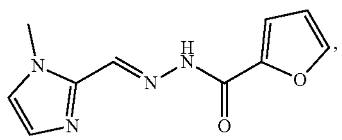

(VII)

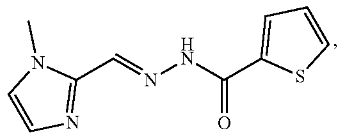

or pharmaceutically acceptable salts thereof.

11. A pharmaceutical composition, comprising:

a compound of formula (I) as defined in claim 1, or a pharmaceutically acceptable salt thereof, and at least one pharmaceutically suitable excipient.

12. The pharmaceutical composition according to claim 11, wherein the compound of formula (I) has the following formulae (II) or (III):

(II)

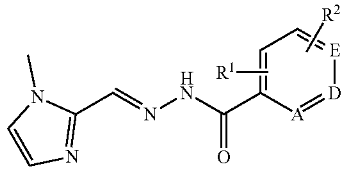

(III)

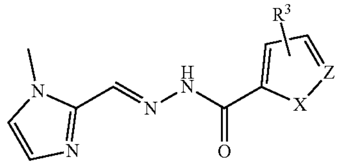

in which:

A represents $CR^4$ or N;

D represents $CR^4$ or N;

E represents $CR^4$ or N;

X represents O, S or NH;

Z represents $CR^4$ or N;

$R^1$ represents a hydrogen, a halogen, an alkyl group, an alkoxyl group, an ester group, an acyl group, a phenoxyl group, a cyano group, a nitro group, a hydroxyl group, or a thioalkoxyl group;

$R^2$ represents a hydrogen, a halogen, an alkyl group, an alkoxyl group, an ester group, an acyl group, a phenoxyl group, a cyano group, a nitro group, a hydroxyl group, or a thioalkoxyl group;

$R^3$ represents a hydrogen, a halogen, an alkyl group, an alkoxyl group, an ester group, an acyl group, a phenoxyl group, a cyano group, a nitro group, a hydroxyl group, or a thioalkoxyl group; and $R^4$ a hydrogen, a halogen, an alkyl group, an alkoxyl group, an ester group, an acyl group, a phenoxyl group, a cyano group, a nitro group, a hydroxyl group, or a thioalkoxyl group, or a pharmaceutically acceptable salt thereof, with the proviso that at least one of A, D or E represents N.

13. The pharmaceutical composition according to claim 12, wherein the compounds of formulae (II) or (III) are one of the compounds of formulae (IV), (VI) or (VII):

(IV)

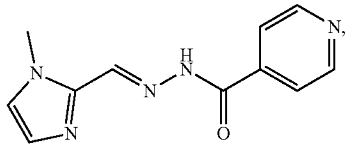

(VI)

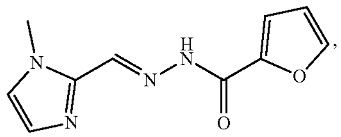

(VII)

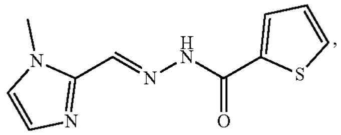

or pharmaceutically acceptable salts thereof.

14. A method for treating amyloid or non-amyloid degenerative aggregopathy, comprising:

administering, to a subject in need thereof, the N-acylhydrazonic compound of claim 2, or a pharmaceutically acceptable salt thereof, as an active component.

15. A method for treating amyloid or non-amyloid degenerative aggregopathy, comprising:

administering, to a subject in need thereof, the N-acylhydrazonic compound of claim 3, or a pharmaceutically acceptable salt thereof, as an active component.

16. A method for treating amyloid or non-amyloid degenerative aggregopathy, comprising:

administering, to a subject in need thereof, the N-acylhydrazonic compound of claim 4, or a pharmaceutically acceptable salt thereof, as an active component.

17. A method for treating amyloid or non-amyloid degenerative aggregopathy, comprising:

administering, to a subject in need thereof, the N-acylhydrazonic compound of claim 5, or a pharmaceutically acceptable salt thereof, as an active component.

18. A method for treating amyloid or non-amyloid degenerative aggregopathy, comprising:

administering, to a subject in need thereof, the N-acylhydrazonic compound of claim 6, or a pharmaceutically acceptable salt thereof, as an active component.

* * * * *